United States Patent [19]

Yount

[11] Patent Number: 5,099,855

[45] Date of Patent: Mar. 31, 1992

[54] METHODS OF AND APPARATUS FOR MONITORING RESPIRATION AND CONDUCTIVE GEL USED THEREWITH

[75] Inventor: John E. Yount, Beaverton, Oreg.

[73] Assignee: State of Oregon, acting by and through the Oregon State Board of Higher Education, acting for and on behalf of the Oregon Health Sciences University, Portland, Oreg.

[21] Appl. No.: 433,705

[22] Filed: Nov. 9, 1989

[51] Int. Cl.⁵ .............................................. A61B 5/08
[52] U.S. Cl. .................................... 128/721; 128/782
[58] Field of Search ............... 128/721, 722, 723, 782, 128/774; 324/691, 699; 338/80, 94, 99, 114, 231

[56] References Cited

U.S. PATENT DOCUMENTS

| | | |
|---|---|---|
| 2,194,809 | 3/1940 | Powell .................................. 128/721 |
| 2,518,906 | 8/1950 | Kocmich ............................... 338/114 |
| 2,671,153 | 3/1954 | Ray et al. ............................. 338/114 |
| 3,268,845 | 8/1966 | Whitmore ............................ 128/721 |
| 3,419,702 | 12/1968 | Piel ........................................ 338/114 |
| 4,308,872 | 1/1982 | Watson et al. ....................... 128/721 |

Primary Examiner—Kyle L. Howell
Assistant Examiner—Kevin Pontius
Attorney, Agent, or Firm—Millen, White & Zelano

[57] ABSTRACT

An apparatus for measuring respiration includes a first gauge for positioning around a patient's chest and a second gauge for positioning around the patient's abdomen. Each gauge is comprised of a silicone rubber tube filled with a conductive gel. The conductive gel is a composition comprising glycerol, water, and sodium chloride. Upon securing the gauges about the patient, signals indicative of absolute volume are immediately available, providing a new and improved method of measuring and/or monitoring respiration.

20 Claims, 5 Drawing Sheets

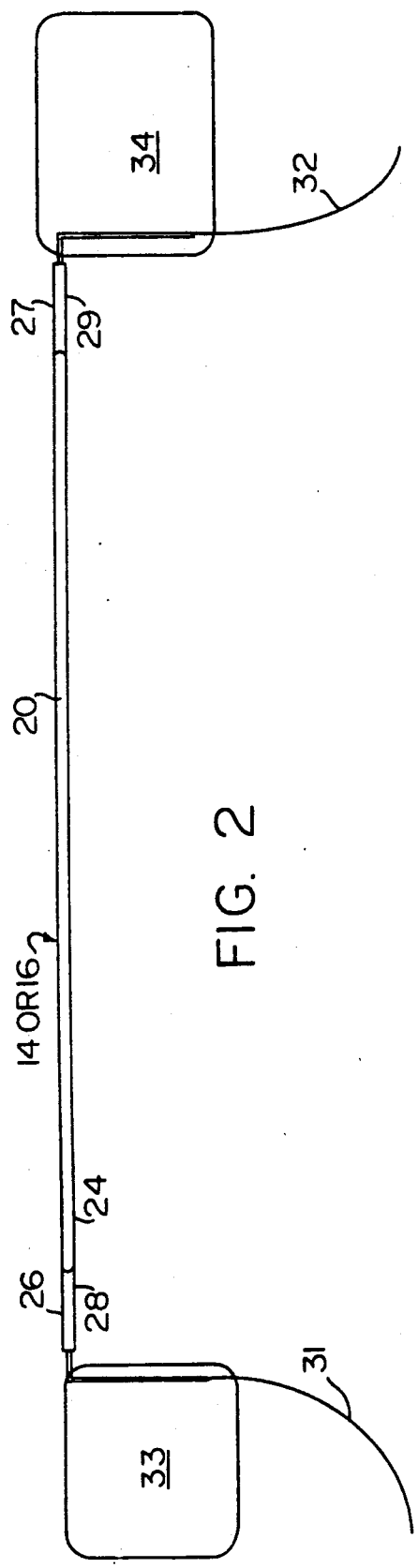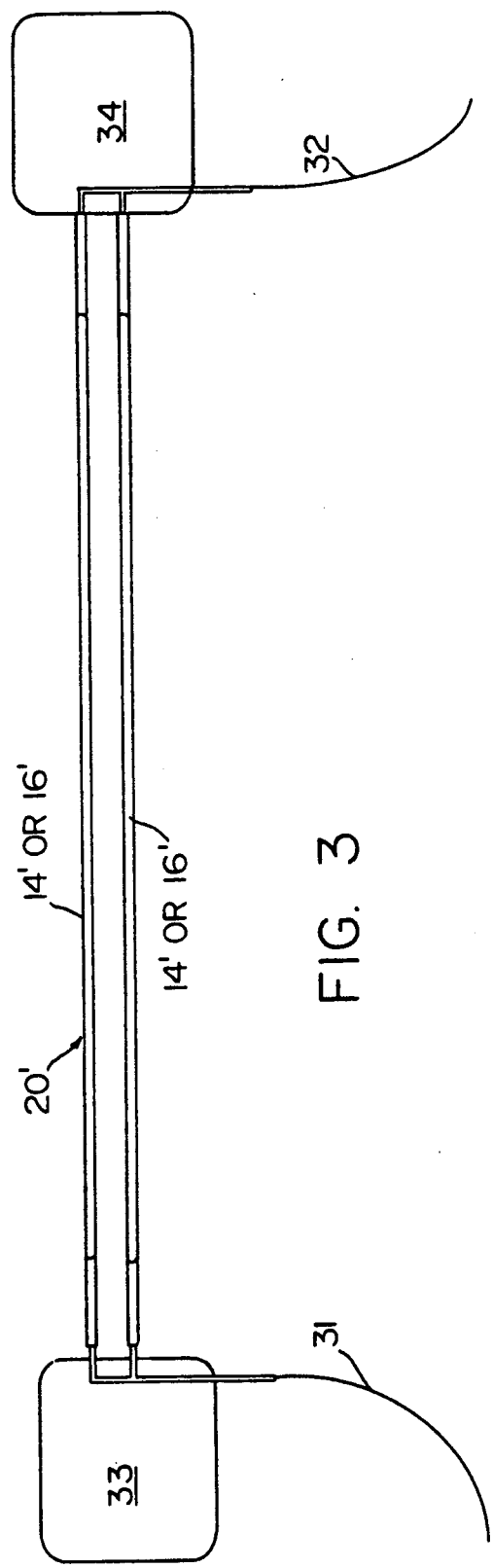

METHODS OF AND APPARATUS FOR MONITORING RESPIRATION AND CONDUCTIVE GEL USED THEREWITH

BACKGROUND OF THE INVENTION

The instant invention relates to apparatus and a process for monitoring respiration as well as to a conductive gel used therewith, wherein the apparatus comprises at least first and preferably second circumferential gauges that attach around a patient's abdomen and chest to monitor expansion thereof as the patient breaths. The gauges are configured as hollow tubes containing the new and improved conductive gel.

In the past, continuous volumetric monitoring of patients' ventilation generally involved use of face masks or mouthpieces, approaches which are not only invasive and uncomfortable to the patient but also interfere with the very breathing patterns being measured. These approaches required considerable cooperation from patients, which cooperation was compromised if the patient was critically ill, comatose, or very young. In addition, leaving mouthpieces in place was a danger in and of itself in that mouthpieces can suffocate patients. Utilizing these invasive methods required constant supervision and attention, further limiting the desirability of these techniques.

In view of such deficiencies, noninvasive techniques were developed such as those exemplified in U.S. Pat. Nos. 3,268,845 and 3,483,861, wherein respiration is monitored by measuring expansion of the patient's torso at primary levels of respiration; namely, expansion of the thoracic cavity, diaphragm, and abdomen. A current approach is shown in U.S. Pat. No. 4,373,534, wherein inductive loops are positioned around the thoracic cavity and abdomen. As the patient breathes, the inductive loops expand and contract, resulting in changes in cross-sectional area and inductance of the loops. Monitoring these changes provides a measure of respiration volume. This has been performed in research for a number of years, using mercury in rubber gauges. The art has continued to progress to current approaches, wherein elastic tubes containing mercury or aqueous solutions are used. Mercury is a material which should, if possible, be avoided since exposure to mercury presents a severe health hazard.

As was pointed out in Brouillette et al., "Comparison of Respiratory Inductive Plethysmography and Thoracic Impedance for Apnea Monitoring," *Journal of Pediatrics*, September 1987, pp. 377–383, incorporated herein by reference, respiratory inductive plethysmographs have advantages over conventional thoracic impedance monitors for infants. Plethysmographs need to be substantially modified before being used for routine monitoring of infants in hospitals or at home. Moreover, the cost is excessive and the associated systems complex.

One approach has been to use natural rubber tubes containing a conductive aqueous solution. However, rubber tubes containing aqueous solutions have been found to have a limited shelf-life of six to ten months and an active life of only 48 hours. Accordingly, they are only useful for overnight diagnostic recordings. Continuous monitoring over several days using such tubes results in considerable expense, since the tubes must be replaced repeatedly. The concept of a rubber tube with an aqueous solution has the advantage of generating very clear signals with low noise generated by physiological and electronic interference. Apparently, the shelf-life of these devices in a Mylar storage envelope and active life after the envelope is opened is limited by passage of the aqueous solution through the walls of the gauge.

Another general deficiency of prior art devices is that these devices are incapable of obtaining rapid, quantitative, absolute measurements which are accurate.

In view of the aforementioned considerations, there is a need for an improved apparatus and method which monitors respiration with accuracy and absolute values, which apparatus has signal-to-noise ratio advantages of currently available natural tubes with aqueous electrolytes, yet have both extended shelf-life and extended active life.

SUMMARY OF THE INVENTION

In the apparatus aspect of the invention, there is provided apparatus for detecting expansion and contraction of a body, comprising:

an elastic tube having first and second sealed ends and containing therein a conductive gel comprising glycerol, water, and at least one conductive salt contained within the tube, which gel changes in inductance as the tube is stretched; and first and second connectors at first and second ends of the tube in electrical contact with the gel, wherein as the tube stretches, changes in the inductance thereof is measured by current flowing between the contacts through the conductive gel.

The instant invention further contemplates a conductive fluid or gel containing water and glycerol, 35–90% by volume and preferably 50–70% by volume and at least one of the following salts: NaCl, preferably from about 20% (g/100 ml) by volume to saturated solution; KCl, preferably from about 20% (g/100 ml) by volume to saturated solution; and sodium or potassium acetate, preferably from about 20% (g/100 ml) by volume to saturated solution; calcium lactate, preferably from about 20% (g/100 ml) by volume to saturated solution; and magnesium sulfate, preferably from about 20% by volume to saturated solution. It is particularly preferred that the salts be present as a saturated solution.

The instant invention further contemplates an apparatus for measuring tidal volume noninvasively by encircling a patient's chest and abdomen with at least one silicone rubber tube filled with a nontoxic hygroscopic electrolyte. Each tube has first and second ends sealed with first and second electrical contacts which are in contact with the electrolyte. As the tubes stretch, the impedance of the electrolyte changes. This change in impedance is detected by changes in pulsed current flowing through the electrolyte between the contacts as measured in a constant amperage circuit.

Upon further study of the specification and appended claims, further objects and advantages of this invention will become apparent to those skilled in the art.

BRIEF DESCRIPTION OF THE DRAWINGS

Various other objects, features, and attendant advantages of the present invention will be more fully appreciated as the same becomes better understood when considered in conjunction with the accompanying drawings in which like reference characters designate the same or similar parts throughout the several views, and wherein:

FIG. 2 is a planar view of one gauge of the instant invention shown in its relaxed state before being attached to the patient;

FIG. 3 is a planar view of a second embodiment of the gauge having a pair of silicone rubber tubes, rather than a single tube;

DETAILED DESCRIPTION

Figure 1:
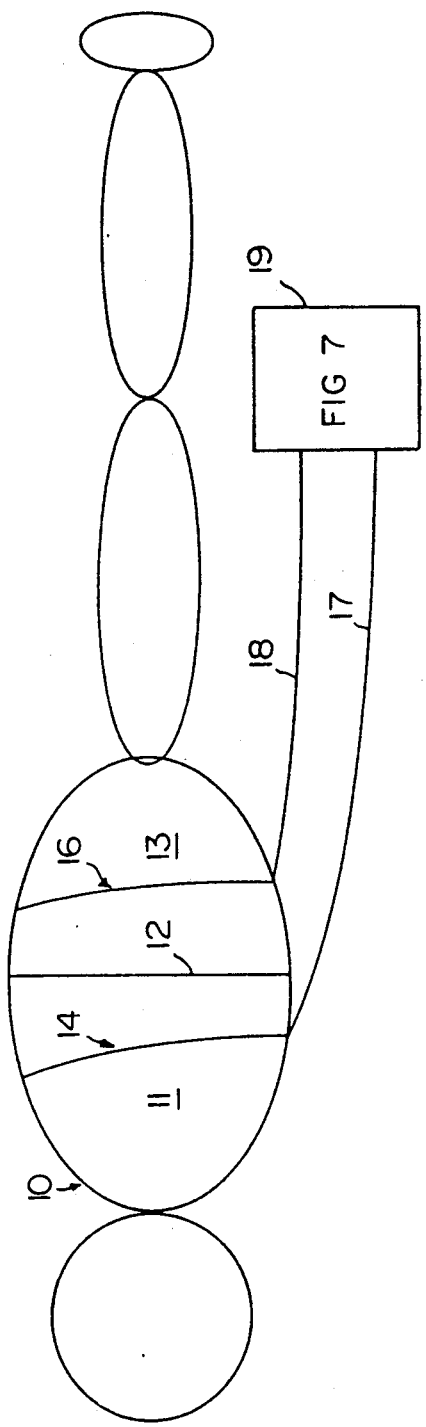
FIG. 1 is a diagram showing attachment of the apparatus of the instant invention to a patient.

Referring now to FIG. 1, there is shown a patient designated generally by the numeral 10 having a chest or thorax 11, a diaphragm generally illustrated by the numeral 12; and an abdomen 13. A chest gauge, designated generally by the numeral 14, having the configuration of the gauges shown in FIGS. 2 and 3, is tensioned around the patient's chest 11, while an abdominal gauge designated generally by the numeral 16, also having the configuration of the gauges shown in FIGS. 2 and 3 is tensioned around the patient's abdomen. In other words, the chest gauge 14 is positioned above the patient's diaphragm 12, while the abdominal gauge 16 is positioned below the patient's diaphragm. The gauges 14 and 16 are connected via leads 17 and 18 to a monitoring circuit, designated generally by the numeral 19 and illustrated more specifically in FIG. 8.

Referring now to FIG. 2, there is shown one embodiment for the gauges 14 or 16, wherein a silicone rubber tube 20 having a length in the range of 16-36 cm, a wall thickness of 0.003", and an inside diameter of 2 mm is filled with a conductive gel 24 so as to have mechanical and electrical characteristics similar to gauges using a mercury conductor. The tube 20 is sealed at first and second ends 26 and 27 by bronze or gold L-shaped contacts 28 and 29, respectively, which are soldered to standard patient lead wire connectors 31 and 32. Velcro TM pads 33 and 34 are bonded or otherwise connected to the L-shaped contacts 28 and 29 so that the gauges 14 and 16 attach securely about the patient's thorax and abdomen.

Referring now to FIG. 3, there is shown an alternative embodiment of the invention, wherein the silicone rubber tubing 20 is arranged in pairs with identical tubes 20A and 20B, each having substantially the same characteristics as the tube 20 of FIG. 2.

Gel 24 is a mixture of the following substances:
glycerol in the range of about 35-90% by volume and preferably about 40-70% by volume mixed with water;
NaCl, from about 20 g per 100 ml by volume to preferably a saturated solution;
KCl, from about 20 g per 100 ml by volume to preferably a saturated solution;
potassium acetate, from about 20 g per 100 ml by volume to preferably a saturated solution;
calcium lactate, from about 20 g per 100 ml by volume to preferably a saturated solution;
magnesium sulfate, from about 20 g per 100 ml by volume to preferably a saturated solution;
optional ingredients: glucose, 1 g to 50 g per 100 ml by volume and commercial, nontoxic food coloring.

A satisfactory method for making the gel is to start with water and to add NaCl to saturation, then add KCl to saturation, K acetate to saturation, calcium lactate to saturation, and, if a gel is desired, magnesium sulfate to saturation. In every instance, saturation is observed by the presence of an undissolved solid phase of the added component. Thereafter, the glycerol is added and, after the volume of glycerol exceeds a value of about 40%, undissolved salts surprisingly enter into the solution, thereby resulting in a system having salt concentrations exceeding those in water alone. It is contemplated that other methods may also be used, e.g., adding the salts to a glycerol-water mixture. In any case, an important inventive aspect of this invention is the discovery of the enhanced salt solubilities due to the presence of glycerol, and it is contemplated that equivalent salt mixtures or even single salts may be used to obtain advantages of the invention.

All of the above components are commonly used materials which are available for intravenous fluid preparations and are readily available in sterile form. The solution does not support bacterial growth without glucose. If glucose is included, it is preferred that a mixture be made up in a closed, sterile circuit. Since the mixture is normally a clear gel, the addition of food coloring helps in determining if the contacts are immersed and whether the tube is completely filled with gel so as to preclude air spaces or voids. In addition, since the silicone rubber tubes 14 and 16 have very thin walls, e.g., as low as 0.003 inch, the addition of food coloring indicates whether the walls have been ruptured or whether there has been passage of any of the gel or its constituents through the tubing wall by osmosis. Another advantage of the aforedescribed gel is that it may be stored for an indefinite period without leaking through the tube wall and thereafter serve as a stable transducer for at least a month or more while maintaining impedance below about 80 kohms.

Figure 4A:
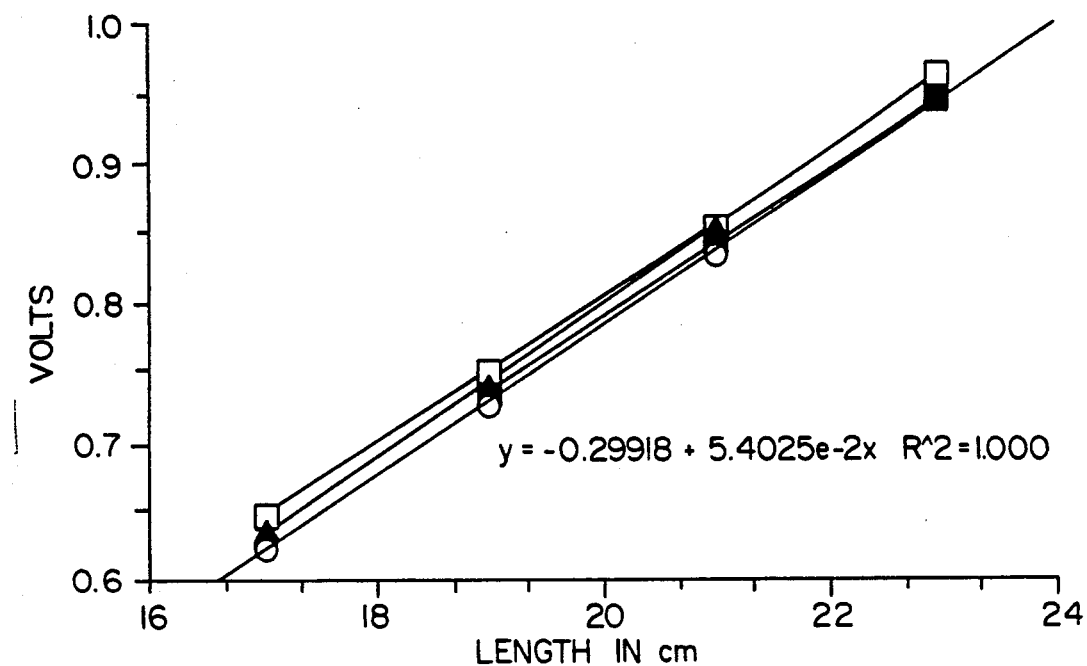
FIGS. 4A and 4B are graphs illustrating change in voltage as a function of tube stretch.
Figure 5:
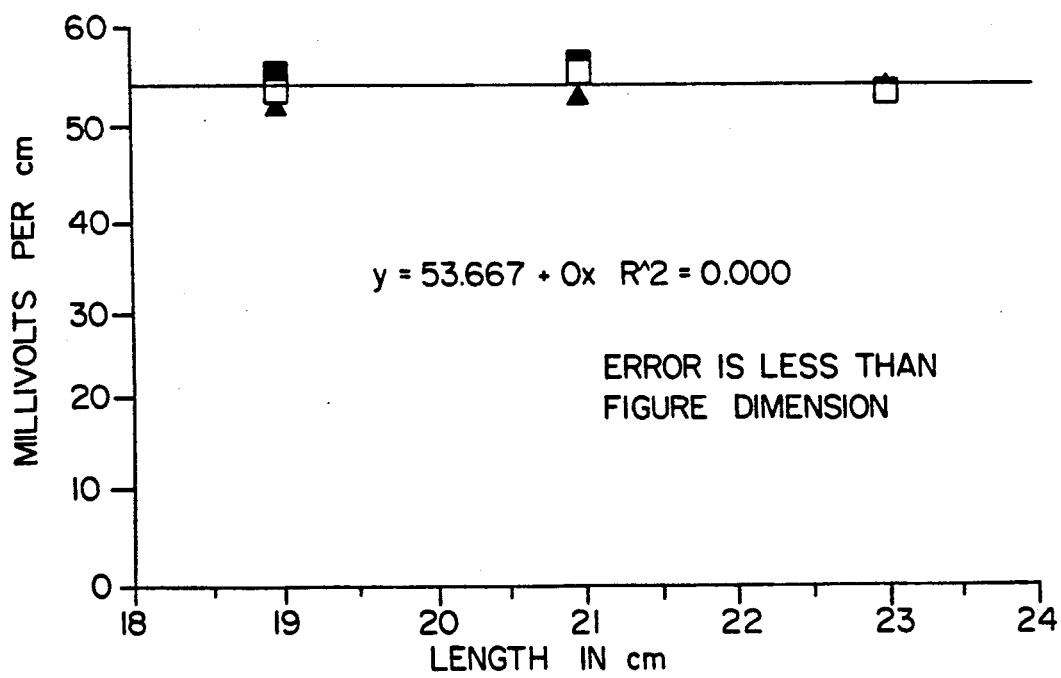
FIG. 5 is a graph illustrating that the voltage rate in millivolts/centimeter remains substantially constant between 18-24 cm when the tube in accordance with the instant invention is in a relaxed state.
Figure 4B:
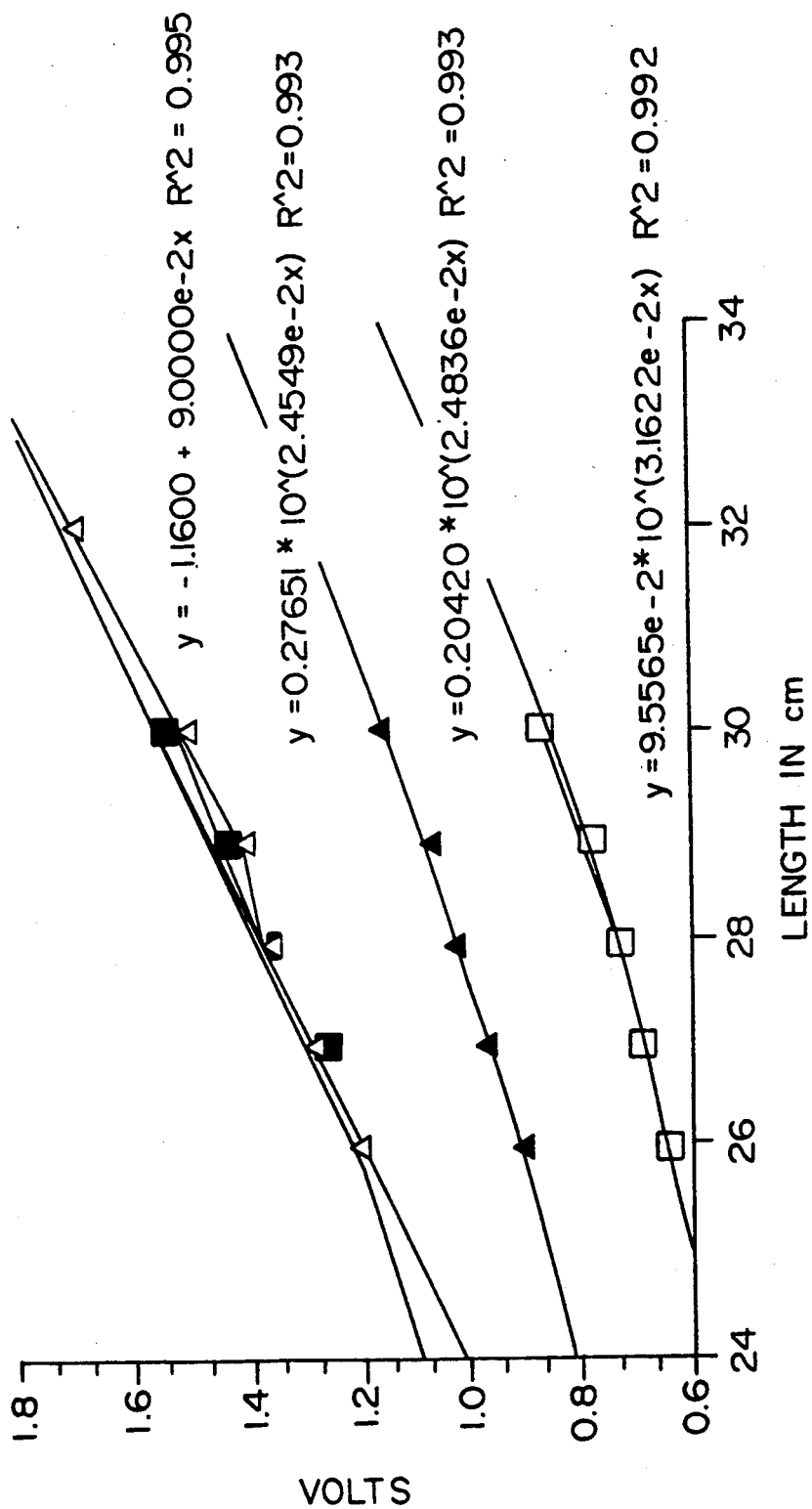

Depending on its geometry, the impedance of the gauges 14 and 16 is in the range of 20-60 kohms, with voltage/centimeter remaining substantially constant at different gauge lengths, as is illustrated in FIG. 5. As is seen by extrapolating FIGS. 4A and 4B, the change in impedance with stretch is nearly linear for at least 50% of the length of the gauge. The signal-to-noise ratio is high, with more than 300 mv/cm of stretch when activated by 2-4 volts applied in the range of 500 Hz to 30 kHz. Gauges 14 and 16 are capable of resolving a 0.1 mm change in dimension with a battery-powered circuit. Since the circumferential respiratory excursion for adults is usually less than 6 cm (0.1 mm to 60 mm), the gauge provides a highly accurate indicator of tidal volume.

By simultaneous cross-sectional measurements of the patient's thorax or chest 11 with the gauge 14 and the patient's abdomen 13 with the gauge 16, approximations of tidal volume accurate to 0.1 mm of gauge length can be obtained. Since the absolute circumference is known, the variation in circumference can be used to estimate volume based on coefficients determined in vivo by one obstruction performed during inspiration and another performed during expiration. The relationship of tidal volume to circumference is a unique coefficient relating volume to the square of the circumference of the applied gauges 14 and 16. The interaction of the thorax 11 and the abdomen 13 is calculated simultaneously in real time to estimate both tidal volume and functional residual capacity. Since the signal from the gauge provides both absolute circumference and circumference variation to an accuracy of 0.1 mm, an estimate of both functional residual capacity and tidal volume can be developed to a presumed accuracy of a few cubic centimeters. By using the two gauges 14 and 16 in fixed geometry around the patient, an independently calibratable monitor for absolute volume of respiratory effort is provided. The gauges 14 and 16 can be manufactured to tolerances where the impedance is calculable simply by knowing the gauge geometry.

Figure 6:
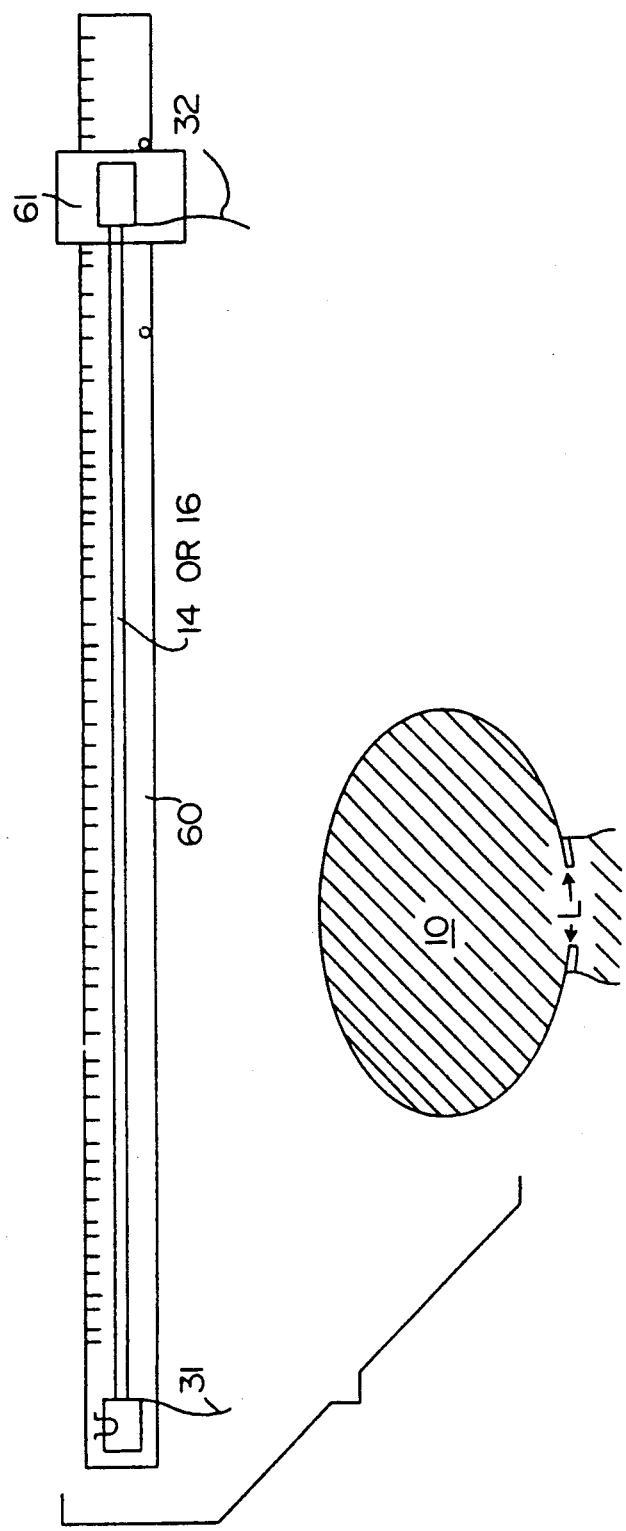
FIG. 6 is a diagram showing how the tubular gauges of the instant invention are calibrated.

Referring now to FIG. 6, there is shown apparatus for performing the calibrating step of the instant invention, wherein gauge 14 or 16 is mounted on an accurate vernier rule 60 by fixing one end 26 thereto and attaching the other end 27 to a sliding element 61 settable to fixed stops. The gauge 14 or 16 is then stretched to measured lengths and the voltage levels indicative of these lengths is entered into the microprocessor 19 (FIGS. 1 and 7) via a standard digital switch.

In order to obtain an accurate average signal, the gauge 14 or 16 may be stretched a number of times between fixed stops and the voltages at those stops entered in and averaged by the microprocessor 9.

The gauge 14 or 16 is then wrapped around a patient 10 and the separation distance "L" entered in the microprocessor 19 as a correction factor via a digital switch. The distance "L" is added to the lengths of the gauges 14 and 16 so that the total circumference of the patient is taken into account when computing residual capacity and tidal volume of the patient's respiration.

By utilizing the aforedescribed gauges 14 and 16, one is able to obtain immediately a reading of absolute volume and need not wait the usual ten minutes for a system using induction loops to average out readings and settle down to a reasonable approximation of volume. Accordingly, the gauges 16 and 17 of the instant invention allow for faster more efficient utilizations of systems such as NMR's and CT's.

Figure 7:
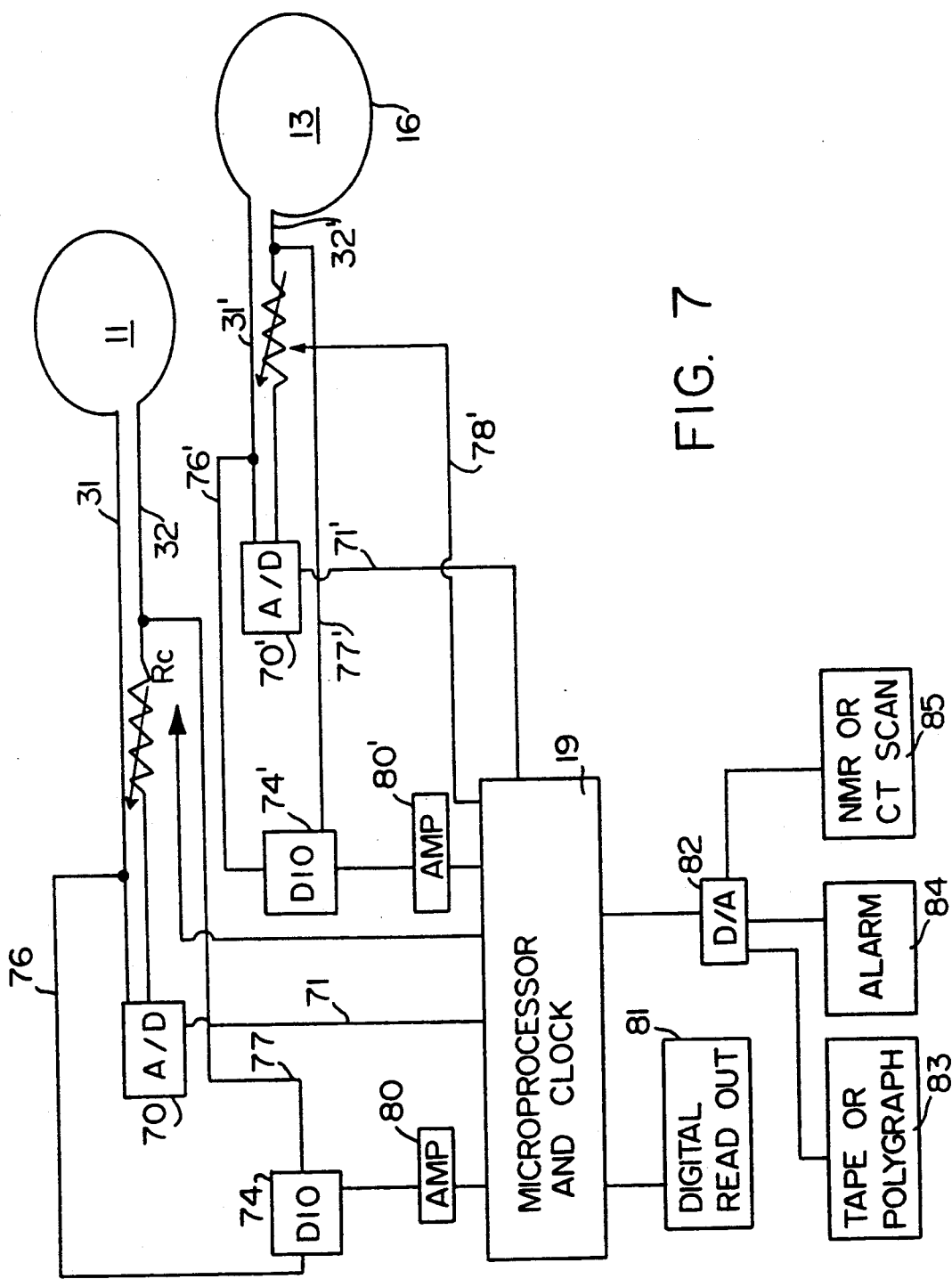
FIG. 7 is a schematic diagram of a circuit for processing information from the tubular gauges shown applied to the patient in FIG. 1.

Referring now to FIG. 7, it is seen that the chest gauge 14 and abdominal gauge 16 are connected to the microprocessor and clock 19. Leads 31 and 31' of the gauges 14 and 16, respectively, are connected through analog-to-digital converters 70 and 70' to the microprocessor and clock 19 via leads 71 and 71'. Leads 32 and 32' are connected to the analog-to-digital converters 70 and 70' via variable resistors Rc and Ra, respectively, and their input is also fed to the microprocessor 19 via lines 71 and 71'. The signals on lines 31 and 31', and 32 and 32' are fed through digital input-output chips 74 and 74' via lines 76 and 76', and 77 and 77', respectively, with the signals on lines 77 and 77' being unmodified by the resistors Rc and Ra in series with the gauges and while changes in pulse amplitude are measured through programmable input amplifiers 80 and 80'.

The output of the microprocessor 19 can be displayed by a digital readout 81, or via a digital-to-analog converter 82, recorded on tape or by a polygraph 83. The signal from the digital-to-analog converter 82 may also sound an alarm 84 or be used to enhance NMR or CT scan images 85.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

The entire texts of all applications, patents and publications cited herein are hereby incorporated by reference.

What is claimed is:

1. A silicone tube useful as a linearly stretchable respiratory gauge having minimal response to proximate high frequency electromagnetic fields, containing a composition of about 40% by volume glycerol and about 60% by volume water and sodium chloride in a concentration of from about 20 grams per 100 ml of solution to saturation.

2. A silicone tube according to claim 1, the composition further comprising potassium chloride.

3. A silicone tube according to claim 2, the composition further comprising calcium lactate.

4. A silicone tube according to claim 1, the composition further comprising potassium acetate.

5. A silicone tube according to claim 4, the composition further comprising calcium lactate.

6. A silicone tube according to claim 5, wherein all the salts of the composition are present as a saturated solution thereof in a higher concentration than with water alone.

7. A silicone tube according to claim 6, the composition further comprising a gel-forming concentration of magnesium sulfate.

8. A silicone tube according to claim 1, the composition further comprising calcium lactate.

9. A silicone tube according to claim 1, the composition further comprising a gel-forming concentration of magnesium sulfate.

10. The silicone tube of claim 1, the composition being a fluid.

11. The silicone tube of claim 1, the composition being a gel.

12. An apparatus for monitoring respiration of mammals comprising first tubular gauge means for surrounding the chest of the mammal and second tubular gauge means for surrounding the abdomen of the mammal, each gauge means comprising at least one stretchable silicone rubber tube filled with conductive gel, the conductive gel being in electrical contact with a pair of electrical contacts disposed within opposite ends of the tubes, means for applying signals indicative of changes in impedance of the tubes as the tubes stretch to signal processing means wherein immediate, absolute calculation of the thoracic volume is achieved, the tubes being of a length and wall thickness and the conductive gel being of a composition which are each selected to provide a substantially linear change in impedance per unit of stretch.

13. The apparatus of claim 12, wherein the first and second tubular gauge means each comprise a pair of silicone rubber tubes filled with the conductive gel.

14. The apparatus of claim 13, wherein the silicone tubes each have a length in the range of 16 to 36 cm, a wall thickness in the range of 1 to 6 mills, and an inside diameter in the range of 1 to 3 mm, and wherein the conductive gel within each tube is a composition comprising 35 to 90% by volume glycerol, 65-10% by volume water, and sodium chloride of from about 20 grams per 100 ml of solution to saturation.

15. The apparatus of claim 12, wherein the silicone tube has length in the range of 16 to 36 cm, a wall thickness in the range of 1 to 6 mills, and an inside diameter in the range of 1 to 3 mm and wherein the conductive gel is a composition comprising 35 to 90% by volume glycerol, 65-10% by volume water, and sodium chloride of from about 20 grams per 100 ml of solution to saturation.

16. A process for measuring respiration of a patient comprising:
  calibrating first and second tubular gauges of silicone rubber filled with a conductive gel by stretching the gauges and storing voltage readings indicative of changes in impedance in a microprocessor, and
  tensioning the first tubular gauge and securing the tensioned gauge about the patient's chest, tensioning the second tubular gauge and securing the tensioned gauge about the patient's abdomen, and measuring changes in impedance in each gauge as the gauge expands and contracts in length due to respiration of the patient in order to monitor the patient's respiration.

17. The process of claim 16, wherein a measurement of absolute volume of respiratory effort is available immediately because the gauges are calibrated prior to attachment to the patient.

18. An apparatus for monitoring respiration of mammals comprising first tubular gauge means for surrounding the chest of the mammal and second tubular gauge means for surrounding the abdomen of the mammal, each gauge means comprising at least one silicone rubber tube filled with conductive gel, the silicone rubber tubes comprising the gauge means each having a length in the range of 16 to 36 cm, a wall thickness in the range of 1 to 6 mills, and an inside diameter in the range of 1 to 3 mm, the conductive gel within each tube being a composition comprising 35 to 90% by volume glycerol, 65-10% by volume water, and sodium chloride of from about 20 grams per 100 ml of solution to saturation, the conductive gel being in electrical contact with a pair of electrical contacts disposed within opposite ends of the tubes, signal processing means for applying and means for applying signals indicative of changes in impedance of the tubes to said signal processing means wherein immediate, absolute calculation of thoracic volume is achieved.

19. The apparatus of claim 18, wherein the first and second tubular gauge means each comprise a pair of silicone rubber tubes filled with the conductive gel.

20. The apparatus of claim 18, wherein the composition is about 40% by volume glycerol.

* * * * *